United States Patent
Bosch et al.

(10) Patent No.: US 6,245,917 B1
(45) Date of Patent: Jun. 12, 2001

(54) CRYSTALLINE SODIUM PHENYTOIN MONOHYDRATE

(75) Inventors: Robert Lee Bosch, Allendale, MI (US); Peter Raymond Johnson, West Lafayette, IN (US); Robert Joseph Stahl, Holland, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/297,545

(22) PCT Filed: Dec. 15, 1998

(86) PCT No.: PCT/US98/26703

§ 371 Date: May 3, 1999

§ 102(e) Date: May 3, 1999

(87) PCT Pub. No.: WO99/48876

PCT Pub. Date: Sep. 30, 1999

Related U.S. Application Data (60) Provisional application No. 60/078,804, filed on Mar. 20, 1998.

(51) Int. Cl.[7] ............... C07D 233/74; A61K 31/4166
(52) U.S. Cl. ........................... 548/321.1; 514/398
(58) Field of Search .................. 548/321.1; 514/398

(56) References Cited

U.S. PATENT DOCUMENTS

| 2,242,775 | | 5/1941 | Bywater | 260/309 |
|---|---|---|---|---|
| 2,409,754 | | 10/1946 | Henze | 260/309.5 |
| 2,409,755 | * | 10/1946 | Henze | 548/321.1 |
| 2,409,756 | * | 10/1946 | Henze | 548/321.1 |
| 2,684,371 | * | 7/1954 | Levy | 548/321.1 X |
| 4,304,782 | * | 12/1981 | Dumont et al. | 424/273 R |
| 4,642,316 | | 2/1987 | Fawzi et al. | 514/398 |
| 4,696,814 | | 9/1987 | Kao et al. | 424/80 |

OTHER PUBLICATIONS

The Merck Index, Twelfth Edition, p. 1260, No. 7475, 1996.*

* cited by examiner

*Primary Examiner*—Floyd D. Higel
(74) *Attorney, Agent, or Firm*—Charles W. Ashbrook (57) ABSTRACT

Crystalline sodium phenytoin monohydrate is stable, nonhygroscopic, and water soluble.

12 Claims, 4 Drawing Sheets

CRYSTALLINE SODIUM PHENYTOIN MONOHYDRATE

This application is filed under 35 U.S.C. § 371 from PCT/US98/26703 filed Dec. 15, 1998, which claims benefit of provisional application Ser. No. 60/078,804 filed Mar. 20, 1998.

FIELD OF THE INVENTION

This invention relates to a crystalline form of sodium phenytoin monohydrate, to pharmaceutical formulations containing the same, and to methods for preparing and using the substance.

BACKGROUND OF THE INVENTION

Phenytoin is the generic name for 5,5-diphenyl-2,4-imidazolidinedione. It also is known as diphenylhydantoin. It is used extensively to treat convulsive disorders such as epilepsy. Because phenytoin is poorly soluble in aqueous mixtures, it cannot be effectively used in injectable solutions, or even in solid preparations for oral use. The compound generally is utilized as a sodium salt, which is readily soluble in water. However, even sodium phenytoin anhydrate rapidly dissociates into phenytoin, which then precipitates from aqueous solutions, thereby making uniform dosing difficult. Moreover, commercial production of sodium phenytoin anhydrate results in complex mixtures of polymorphic forms of the product, and the individual polymorphs exhibit different aqueous solubilities and dissolution rates, thereby further exacerbating dosing irregularities. To date, there has been no single crystal form of any phenytoin sodium capable of analysis by x-ray diffraction.

An object of this invention is to provide a new chemical substance that is a crystalline form of a monohydrate of sodium phenytoin. The new compound can be crystallized into a single crystal form which can readily be analyzed by x-ray diffraction. The sodium phenytoin monohydrate crystal form of this invention is stable for prolonged periods of time, and it exhibits excellent aqueous solubility characteristics, thereby allowing for improved uniformity of dosing. The new chemical compound is readily formulated for both oral and parenteral administration to humans for treatment of epilepsy and other convulsive disorders.

SUMMARY OF THE INVENTION

This invention provides a new chemical substance which is a crystalline form of sodium phenytoin monohydrate. The crystal form has a characteristic and unique x-ray diffraction pattern. The invention also provides a pharmaceutical composition comprising the crystalline sodium phenytoin monohydrate admixed with a carrier, diluent, or excipient therefor. The invention additionally provides a method for preparing the crystal form, as well as a method for treating convulsant disorders comprising administering an anticonvulsive effective amount of the crystal form. The crystal form can also be used to stabilize polymorphic mixtures of sodium phenytoin.

In a preferred embodiment, the sodium phenytoin monohydrate crystal form has the following distinctive x-ray pattern (2-theta values measured using $CuK_\alpha$ radiation:

| 2-Theta | d (Å) | Relative Intensities (I) |
|---------|-------|--------------------------|
| 12.1 | 7.3 | 100 |
| 27.2 | 3.3 | 80 |
| 22.7 | 3.9 | 73 |
| 15.5 | 5.7 | 71 |
| 18.4 | 4.8 | 67 |
| 20.3 | 4.4 | 60 |
| 21.2 | 4.2 | 54 |
| 6.2 | 14.2 | 49 |

In a more preferred embodiment, the crystal form of this invention is identified by the following 2-theta values measured using $CuK_\alpha$ radiation: 12.1, 18.4, and 21.2.

In the most preferred embodiment, the crystal form is identified by the following unique 2-theta value measured using $CuK_\alpha$ radiation: 12.1.

DETAILED DESCRIPTION OF THE INVENTION

The crystalline sodium phenytoin monohydrate provided by this invention is prepared by mixing sodium phenytoin with one molar equivalent or slight excess of water in dichloromethane, toluene, or methanol. The mixture typically is heated to a temperature of about 30° C. to about 40° C. for a period of time of about 30 minutes to about 3 hours or longer. The resulting suspension is cooled to about 25° C., and the crystalline sodium phenytoin monohydrate precipitates and can be collected by filtration. The crystalline product generally is dried for about 1 hour or more, preferably in a vacuum, at about 20° C. to about 30° C. The product so formed is highly stable and crystalline, and is highly water soluble.

The sodium phenytoin anhydrate which is the starting material for making the monohydrate of this invention is prepared by standard commercial processes. Specifically, phenytoin can be prepared by reacting benzophenone with ammonium carbonate in the presence of sodium cyanide. The phenytoin is then dissolved in sodium hydroxide solution, and the water is removed from the mixture by drying in a vacuum oven at a temperature of about 50° C. to about 100° C. The dried cake which results is a complex mixture of a large number of polymorphic forms of sodium phenytoin. The mixture of polymorphs leads to commercial preparations which exhibit inconsistent dissolution profiles, thereby causing irregular dosing characteristics from lot to lot in commercial preparations. We have now discovered that such polymorphic mixtures can be stabilized by adding the crystalline sodium phenytoin monohydrate of this invention at a level of about 1% to about 5% by weight. Such stabilization surprisingly leads to improved dissolution profiles and thus to more uniformity in dosing.

The following specific examples demonstrate the synthesis of the unique crystalline compound of this invention.

In the experiments, infrared spectra were obtained on a Perkin-Elmer 1600 FT IR spectrophotometer. Samples were prepared as KBr disks and scanned from 4000–400 cm$^{-1}$. A polystyrene standard was run prior to sample analyses.

Solid-state, carbon-13 nuclear magnetic resonance (SSNMR) spectra were obtained on a Bruker AX-250, 250 MHZ spectrometer using high-power proton decoupling and cross-polarization with magic-angle spinning at approximately 5 kHz. The magic angle was adjusted using the Br signal of KBr by detecting the side bands as described by Frye and Maciel (*J. Mag. Res.* 1982;48:125).

Approximately 300 mg of sample packed into a canister-design rotor was used for each experiment. The chemical shifts were referenced in the first sample to external tetrakis (trimethylsilyl)silane (methyl signal at 3.50 ppm) and subsequent samples were obtained at the same field settings.

Differential scanning calorimetry (DSC) experiments were performed on a Dupont DSC 2000 and thermogravimetric analyses (TGA) were performed on a Dupont TGA 2000. Nitrogen was used as the purge gas and heating rates were 10° C./minute. Standards were run prior to sample analyses; Sn for DSC and calcium oxalate for TGA.

Study of weight change under controlled humidity conditions, samples were placed in open vials, which were placed in closed controlled-humidity jars. Relative humidities were controlled using saturated aqueous salt solutions: 58% RH, NaBr; 75% RH, (NH$_4$)$_2$SO$_4$; 76%, sodium acetate; 84% RH, KBr.

Dissolutions were carried out in a standard Van-Kel dissolution bath. The medium was either water, 90% water/ 10% ethanol, or 95% water/5% ethanol. For nonintrinsic dissolution experiments, SPM and SPA powders were sieved and fractions that passed through a 75 μm sieve were used. For intrinsic dissolution experiments, tablets were prepared in a standard Woods apparatus by compression of 400 mg of material at 3000 psig for 1 minute.

Each experiment was carried out by placing 900 mL of medium into one of the Van-Kel dissolution vessels and allowing it to equilibrate at 37° C. The test materials were added (powder or tablet) and samples were withdrawn by syringe at the specified times (see Table 4). Each sample was filtered through a 0.2μ nylon syringe filter. Three dissolution experiments were carried out for each lot of suspension.

EXAMPLE 1

Fifty grams of sodium phenytoin anhydrate was dissolved in 300 mL of dichloromethane containing 3.28 g of distilled water. The mixture was heated at reflux for 2 hours. The solution was cooled to 24° C., and the crystalline product was collected by filtration and air dried at 24° C. Karl Fischer analysis showed the crystalline product contained 6.20% water; theory for the monohydrate is 6.16%.

EXAMPLE 2

Fifty grams of sodium phenytoin anhydrate was dissolved in 300 mL of dichloromethane containing 6.5 mL of distilled water. The solution was heated at reflux for 3 hours. After cooling the mixture to 24° C., the solid precipitate was collected by filtration and air dried for 48 hours at 24° C. to provide crystalline sodium phenytoin monohydrate. Karl Fisher assay established 6.2% water content.

EXAMPLE 3

Two hundred thirty-eight grams of sodium phenytoin anhydrate was dissolved in a mixture of 1000 mL of dichloromethane and 31 mL of distilled water. The mixture was heated at reflux for 3 hours, cooled to 24° C., and the precipitate was collected by filtration. The solid was dried in a vacuum at 25° C. for 6 hours to provide sodium phenytoin monohydrate. Karl Fisher analysis established water content of 6.35%, evidencing 1 mol of water.

EXAMPLE 4

Preparation of Sodium Phenytoin Monohydrate (Toluene Slurry)

A mixture of 100 g (0.36 mol) 6of sodium phenytoin anhydrate (SPA), 400 mL of toluene, and 6.6 mL (0.37 mol) of water was stirred rapidly under ambient conditions. After 2 days, about 1 mL of the slurry was filtered, and the resulting solid was found, by XRPD analysis (13-day turnaround), to consist of a mixture of SPA and sodium phenytoin monohydrate (SPM). An additional 0.66 mL (0.037 mol) of water was added, and the slurry was stirred overnight. About 1 mL of the slurry was filtered, and the resulting solid was found, by XRPD analysis (3-day turnaround), to consist of pure SPM. The solids were collected by filtration and allowed to dry in the air to give 93.7 g SPM.

EXAMPLE 5

The crystalline sodium phenytoin monohydrate provided by this invention has the following unique x-ray powder diffraction pattern when measured with a Siemans D-500 X-Ray Power Diffraktometer-Kristalloflex with an IBM-compatible interface, with software known as Diffrac AT (Socabim 1994). The x-rays are from CuK$_\alpha$ radiation (20 mA, 40 kV, λ=1.5406 Å) (Slits I and II at 1°) electronically filtered by a Kevex Psi Peltier Cooled Silicon [Si(Li)] Detector (Slits: III at 1°, IV at 0.15°). A continuous theta-two theta scan at 6°/min (0.4 sec/0.04° step) from 4.00° to 40.00° was used. A silicon standard is run to check the x-ray tube alignment. The sample of crystalline monohydrate was pressed onto a zero-background quartz plate in an aluminum holder. The sample width was 15 mm. The foregoing analysis produced the following 2-theta data, spacings, and relative intensities.

| 2-Theta | Spacing, d(Å) | Relative Intensities, I/I$_1$ |
|---------|---------------|-------------------------------|
| 12.129  | 7.2909        | 100.00                        |
| 27.227  | 3.2727        | 80.38                         |
| 22.685  | 3.9165        | 72.60                         |
| 15.542  | 5.6968        | 70.76                         |
| 18.379  | 4.8234        | 67.28                         |
| 20.259  | 4.3798        | 59.76                         |

-continued

| 2-Theta | Spacing, d(Å) | Relative Intensities, I/I$_1$ |
|---|---|---|
| 21.223 | 4.1830 | 53.97 |
| 6.214 | 14.2105 | 48.83 |
| 23.158 | 3.8377 | 40.99 |
| 17.195 | 5.1526 | 36.52 |
| 20.630 | 4.3019 | 34.49 |
| 31.173 | 2.8668 | 29.10 |
| 24.337 | 3.6544 | 27.54 |
| 32.827 | 2.7260 | 27.32 |
| 19.774 | 4.4861 | 27.15 |
| 16.373 | 5.4093 | 24.13 |
| 24.700 | 3.6013 | 24.02 |
| 17.537 | 5.0528 | 22.00 |
| 31.731 | 2.8177 | 21.75 |
| 28.668 | 3.1114 | 18.17 |
| 11.363 | 7.7805 | 17.00 |
| 28.969 | 3.0797 | 15.93 |
| 33.963 | 2.6374 | 15.15 |
| 29.399 | 3.0355 | 14.73 |
| 32.540 | 2.7494 | 14.52 |
| 23.856 | 3.7269 | 14.30 |
| 34.235 | 2.6171 | 13.95 |
| 35.808 | 2.5056 | 13.77 |
| 34.725 | 2.5812 | 13.24 |
| 28.167 | 3.1655 | 13.02 |
| 38.255 | 2.3508 | 12.60 |
| 36.386 | 2.4671 | 12.49 |
| 25.660 | 3.4687 | 12.03 |
| 26.323 | 3.3829 | 11.96 |
| 16.782 | 5.2785 | 11.75 |

In a preferred embodiment, the crystal form is identified by the following 2-theta lines:

| 2-Theta | d (Å) | Relative Intensities (I) |
|---|---|---|
| 12.1 | 7.3 | 100 |
| 27.2 | 3.3 | 80 |
| 22.7 | 3.9 | 73 |
| 15.5 | 5.7 | 71 |
| 18.4 | 4.8 | 67 |
| 20.3 | 4.4 | 60 |
| 21.2 | 4.2 | 54 |
| 6.2 | 14.2 | 49 |

In a more preferred embodiment, the crystal form of this invention is identified by the following 2-theta values measured using CuK$_\alpha$ radiation: 12.1, 18.4, and 21.2.

In the most preferred embodiment, the crystal form is identified by the following unique 2-theta value measured using CuK$_\alpha$ radiation: 12.1.

EXAMPLE 6

The sodium phenytoin monohydrate (SPM) of this invention has been compared with sodium phenytoin anhydrate (SPA) and shown to have greatly improved stability and physical properties. Both SPM and SPA were analyzed by x-ray powder diffraction (XRPD), infrared (IR) spectroscopy, solid-state nuclear magnetic resonance (SSNMR) spectroscopy, differential scanning calorimetry (DSC) and thermogravimetric analysis (TGA). The XRPD patterns of SPM and SPA are quite different and distinguishable. While the IR and SSNMR spectra of SPM and SPA are different, the differences are subtle. SPM and SPA behave quite differently on both DSC and TGA thermal analyses. SPA undergoes endothermic transitions at 364° C. and 409° C. that are accompanied by a weight loss of 72%. In contrast, SPM undergoes an endothermic transition at about 65° C. that is accompanied by a 5% weight loss, followed by transitions similar to those exhibited by SPA. the low-temperature transition is consistent with loss of water from SPM. the theoretical amount of water contained in SPM is 6.%.

Water uptake/loss characteristics of SPM and SPA were compared. Samples were kept at ambient temperature under various relative humidities (RHs) and were periodically weighed. The results are shown in Tables 1 and 2. It was found that, on reaching constant weight, SPM lost 10% of its weight under all humidities utilized and SPA gained 25% of its weight under all humidities utilized. The fact that SPM loses significant mass under even high humidity conditions is inconsistent with the loss of only water.

A possible cause of the observed weight loss is that some reaction solvent (toluene in this case) from the preparation of SPM remained on the solid and evaporated in the humidity jars. To test this theory, it was decided to prepare SPM, show it to be solvent-free, and repeat the water uptake studies. Dichloromethane was chosen as the organic solvent for the preparation rather than toluene because its lower boiling point should allow it to be removed from the solid more easily and completely. SPM was made by stirring a slurry of SPA and one equivalent of water in dichloromethane for 2 days, then isolation by filtration and air-drying of the solid SPM.

Any residual dichloromethane should evaporate readily from the solid under ambient conditions. To determine if solvent evaporation could be ensured by drying under low-pressure conditions, a portion of the SPM sample was kept under about 1 torr pressure at ambient temperature for 24 hours. XRPD analysis of the resulting solid indicated that it was SPA. Therefore, these conditions caused dehydration and are too severe for dichloromethane evaporation.

The remainder of the SPM sample was allowed to dry in an open jar under ambient conditions for about 1 week. It was then characterized by XRPD elemental analysis, and Karl Fischer (KF) analysis. The results of elemental analyses are shown in Table 3. The sample appears to be pure SPM containing very little, if any, residual solvent.

The water uptake studies were repeated using the remaining solvent free SPM sample, and the results are shown in Tables 4 and 5. Both SPM and SPA increased in weight about 20% when equilibrium was reached (constant weight) at each humidity utilized. The samples were analyzed by XRPD after completion of the water uptake experiments. Each exhibited the same XRPD pattern, which is different from the patterns exhibited by SPM and SPA. Apparently another hydrated crystal form was produced. The nature of this form has not been determined.

TABLE 1

SPM Behavior at Various Relative Humidities

| Time | Sample Weight in g (Change in Starting Weight in g) | | | Time | Sample Weight in g (Change in Starting Weight in g) | | |
|---|---|---|---|---|---|---|---|
| (days) | 58% RH | 75% RH | 84% RH | (days) | 58% RH | 75% RH | 84% RH |
| 0 | 1.5009 | 1.5360 | 1.5374 | 14 | 1.2938 (−0.2071) | 1.3758 (−0.1602) | 1.3855 (−0.1519) |
| 1 | 1.2006 (−0.3003) | 1.2358 (−0.3002) | 1.2421 (−0.2953) | 15 | 1.3045 (−0.1964) | 1.3759 (−0.1601) | 1.3857 (−0.1517) |
| 2 | 1.1763 (−0.3246) | 1.2405 (−0.2955) | 1.2620 (−0.2754) | 16 | 1.3123 (−0.1886) | 1.3771 (−0.1589) | 1.3880 (−0.1494) |
| 3 | 1.1753 (−0.3256) | 1.2928 (−0.2432) | 1.3287 (−0.2087) | 17 | 1.3255 (−0.1754) | 1.3811 (−0.1549) | 1.3928 (−0.1446) |
| 4 | 1.1856 (−0.3153) | 1.3258 (−0.2102) | 1.3671 (−0.1703) | 18 | 1.3323 (−0.1686) | 1.3818 (−0.1542) | 1.3949 (−0.1425) |
| 5 | 1.2016 (−0.2993) | 1.3707 (−0.1653) | 1.3952 (−0.1422) | 23 | 1.3452 (−0.1557) | 1.3833 (−0.1527) | 1.3986 (−0.1388) |
| 7 | 1.2282 (−0.2727) | 1.3862 (−0.1498) | 1.3932 (−0.1442) | 24 | 1.3446 (−0.1563) | 1.3831 (−0.1529) | 1.3991 (−0.1383) |
| 8 | 1.2402 (−0.2607) | 1.3840 (−0.1520) | 1.3915 (−0.1459) | 25 | 1.3439 (−0.1570) | 1.3826 (−0.1534) | 1.3989 (−0.1385) |
| 10 | 1.2618 (−0.2391) | 1.3813 (−0.1547) | 1.3899 (−0.1475) | 28 | 1.3421 (−0.1588) | 1.3814 (−0.1546) | 1.3980 (−0.1394) |
| 11 | 1.2687 (−0.2322) | 1.3797 (−0.1563) | 1.3885 (−0.1489) | 29 | 1.3450 (−0.1559) | 1.3839 (−0.1521) | 1.4013 (−0.1361) |
| 12 | 1.2795 (−0.2214) | 1.3778 (−0.1582) | 1.3869 (−0.1505) | — | — | — | — |
| Percent Change Based on Average of Final Two Weights | | | | | −10% | −10% | −9% |

TABLE 2

SPA Behavior at Various Relative Humidities

| Time | Sample Weight in g (Change in Starting Weight in g) | | | Time | Sample Weight in g (Change in Starting Weight in g) | | |
|---|---|---|---|---|---|---|---|
| (days) | 58% RH | 75% RH | 84% RH | (days) | 58% RH | 75% RH | 84% RH |
| 0 | 1.5457 | 1.5093 | 1.5152 | 14 | 1.7917 (+0.2460) | 1.8860 (+0.3767) | 1.8931 (+0.3779) |
| 1 | 1.5956 (+0.0499) | 1.6010 (+0.0917) | 1.6255 (+0.1073) | 15 | 1.8047 (+0.2590) | 1.8851 (+0.3758) | 1.8923 (+0.3771) |
| 2 | 1.6268 (+0.0811) | 1.6597 (+0.1504) | 1.6851 (+0.1699) | 16 | 1.8144 (+0.2687) | 1.8863 (+0.3770) | 1.8930 (+0.3778) |
| 3 | 1.6671 (+0.1214) | 1.7067 (+0.1974) | 1.7465 (+0.2313) | 17 | 1.8311 (+0.2854) | 1.8900 (+0.3807) | 1.8964 (+0.3812) |
| 4 | 1.6901 (+0.1444) | 1.7360 (+0.2267) | 1.7834 (+0.2682) | 18 | 1.8411 (+0.2954) | 1.8906 (+0.3813) | 1.8969 (+0.3817) |
| 5 | 1.7120 (+0.1663) | 1.7800 (0.2707) | 1.8368 (+0.3216) | 23 | 1.8889 (+0.3432) | 1.8890 (+0.3797) | 1.8966 (+0.3814) |
| 7 | 1.7268 (0.1811) | 1.8620 (+0.3527) | 1.9054 (+0.3902) | 24 | 1.8944 (+0.3487) | 1.8884 (+0.3791) | 1.8956 (+0.3804) |
| 8 | 1.7354 (+0.1897) | 1.8881 (+0.3788) | 1.9065 (+0.3913) | 25 | 1.8995 (+0.3538) | 1.8875 (+0.3782) | 1.8948 (+0.3796) |
| 10 | 1.7550 (+0.2093) | 1.8917 (+0.3824) | 1.9016 (+0.3864) | 28 | 1.9071 (+0.3614) | 1.8842 (+0.3749) | 1.8924 (+0.3772) |
| 11 | 1.7624 (+0.2167) | 1.8904 (+0.3811) | 1.8995 (+0.3843) | 29 | 1.9112 (+0.3655) | 1.8863 (+0.3770) | 1.8951 (+0.3799) |
| 12 | 1.7749 (+0.2292) | 1.8887 (+0.3794) | 1.8964 (+0.3812) | — | — | — | — |
| Percent Change Based on Average of Final Two Weights | | | | | +24% | +25% | +25% |

TABLE 3

Elemental Analyses Results for SPM

|  | % Carbon | % Hydrogen | % Nitrogen | % Water |
| --- | --- | --- | --- | --- |
| Theoretical | 61.64 | 4.48 | 9.59 | 6.16 |
| Found | 61.21 | 4.45 | 9.69 | 6.49 |

TABLE 3

SPM Behavior at Various Relative Humidities

| Time | Sample Weight in g (Change in Starting Weight in g) | | | Time | Sample Weight in g (Change in Starting Weight in g) | | |
| --- | --- | --- | --- | --- | --- | --- | --- |
| (days) | 58% RH | 75% RH | 84% RH | (days) | 58% RH | 75% RH | 84% RH |
| 0 | 1.5057 | 1.5013 | 1.5068 | 12 | 1.6543 (+0.1486) | 1.7809 (+0.1796) | 1.8167 (+0.3099) |
| 1 | 1.5243 (+0.0186) | 1.5483 (+0.0470) | 1.5663 (+0.0595) | 13 | 1.6612 (+0.1555) | 1.7781 (+0.2678) | 1.8158 (+0.3090) |
| 2 | 1.5326 (+0.0269) | 1.5943 (+0.0930) | 1.6227 (+0.1159) | 14 | 1.6690 (+0.1633) | 1.7768 (+0.2755) | 1.8123 (+0.3055) |
| 3 | 1.5441 (+0.0384) | 1.6399 (+0.1386) | 1.6830 (+0.1762) | 15 | 1.6776 (+0.1719) | 1.7768 (+0.2755) | 1.8064 (+0.2996) |
| 4 | 1.5567 (+0.0510) | 1.6832 (+0.1819) | 1.7377 (+0.2309) | 16 | 1.6851 (+0.1794) | 1.7774 (+0.2761) | 1.8029 (+0.2961) |
| 5 | 1.5677 (+0.0620) | 1.7218 (+0.2205) | 1.7869 (+0.2801) | 17 | 1.6917 (+0.1860) | 1.7754 (+0.2741) | 1.7984 (+0.2916) |
| 6 | 1.5774 (+0.0717) | 1.7565 (+0.2552) | 1.8033 (+0.2965) | 21 | 1.7233 (+0.2176) | — | — |
| 7 | 1.5873 (+0.0816) | 1.7887 (+0.2874) | 1.7978 (+0.2910) | 23 | 1.7380 (+0.2323) | — | — |
| 8 | 1.5997 (+0.0940) | 1.7765 (+0.2752) | 1.8000 (+0.2932) | 26 | 1.7582 (+0.2525) | — | — |
| 10 | 1.6242 (+0.1185) | 1.7738 (+0.2725) | 1.8065 (+0.2997) | 35 | 1.7613 (+0.2556) | — | — |
| 11 | 1.6397 (+0.1340) | 1.7781 (+0.2768) | 1.8130 (+0.3062) | 42 | 1.7568 (+0.2511) | — | — |
| Percent Change Based on Average of Final Two Weights | | | | | +17% | +18% | +20% |

TABLE 4

SPA Behavior at Various Relative Humidities

| Time | Sample Weight in g (Change in Starting Weight in g) | | | Time | Sample Weight in g (Change in Starting Weight in g) | | |
| --- | --- | --- | --- | --- | --- | --- | --- |
| (days) | 58% RH | 75% RH | 84% RH | (days) | 58% RH | 75% RH | 84% RH |
| 0 | 1.5087 | 1.5037 | 1.5023 | 12 | 1.7253 (+0.2166) | 1.8234 (+0.3197) | 1.8345 (+0.3322) |
| 1 | 1.5350 (+0.0263) | 1.5618 (+0.0581) | 1.5735 (+0.0712) | 13 | 1.7337 (+0.2250) | 1.8208 (+0.3171) | 1.8311 (+0.3288) |
| 2 | 1.5597 (+0.0510) | 1.6203 (+0.1166) | 1.6353 (+0.1330) | 14 | 1.7425 (+0.2338) | 1.8189 (+0.3152) | 1.8283 (+0.3260) |
| 3 | 1.5880 (+0.0793) | 1.6662 (+0.1625) | 1.6975 (+0.1952) | 15 | 1.7532 (+0.2445) | 1.8183 (+0.3146) | 1.8278 (+0.3255) |
| 4 | 1.6098 (+0.1011) | 1.7140 (+0.2103) | 1.7521 (+0.2498) | 16 | 1.7618 (+0.2531) | 1.8176 (+0.3139) | 1.8272 (+0.3249) |
| 5 | 1.6198 (+0.1111) | 1.7538 (+0.2501) | 1.7972 (+0.2949) | 17 | 1.7680 (+0.2593) | 1.8154 (+0.3117) | 1.8248 (+0.3225) |
| 6 | 1.6295 (+0.1208) | 1.7862 (+0.2825) | 1.8192 (+0.3169) | 21 | 1.7860 (+0.2773) | — | — |
| 7 | 1.6420 (+0.1333) | 1.8091 (+0.3054) | 1.8298 (+0.3275) | 23 | 1.7905 (+0.2818) | — | — |

TABLE 4-continued

SPA Behavior at Various Relative Humidities

| Time (days) | Sample Weight in g (Change in Starting Weight in g) | | | Time (days) | Sample Weight in g (Change in Starting Weight in g) | | |
|---|---|---|---|---|---|---|---|
| | 58% RH | 75% RH | 84% RH | | 58% RH | 75% RH | 84% RH |
| 8 | 1.6574 (0.1487) | 1.8189 (+0.3152) | 1.8324. (+0.3301) | 26 | 1.7905 (+0.2818) | — | — |
| 10 | 1.6884 (+0.1797) | 1.8202 (+0.3165) | 1.8300 (+0.3277) | — | — | — | — |
| 11 | 1.7081 (+0.1994) | 1.8224 (+0.3187) | 1.8329 (+0.3306) | — | — | — | — |
| Percent Change Based on Average of Final Two Weights | | | | | +19% | +21% | +22% |

EXAMPLE 4

The rates of dissolution of SPM and SPA were compared. In preliminary nonintrinsic dissolution experiments both SPM and SPA were found to dissolve rapidly and extensively in water. These studies were conducted by slurrying sieved (<75 µm) sodium phenytoin powder in pure water and measuring the concentrations in solution at various times by HPLC. Unfortunately, solid crystallized from the solutions withdrawn for analysis as they cooled, rendering the data invalid for determination of dissolution rate. Even so, all of the samples withdrawn contained about 5 mg/mL of sodium phenytoin, including those withdrawn 5 minutes after the slurries were prepared. The amount of sodium phenytoin in samples withdrawn at extended reaction times (24 and 72 hours) appeared to be less than the amount found in the earlier samples. A decrease in the concentration of dissolved sodium phenytoin with time is consistent with the reported reaction of sodium phenytoin with acids, even carbonic acid formed by dissolution of atmospheric carbon dioxide in water, to give relatively water-insoluble phenytoin.

The dissolution rates of both SPM and SPA in water were high enough that differences could not be determined by nonintrinsic dissolution experiments in this medium. Since preliminary solubility studies indicated that sodium phenytoin is less soluble in ethanol than it is in water, it was decided to carry out intrinsic dissolutions in ethanol-water mixtures. For intrinsic dissolution experiments, the test material is compressed into a tablet and the tablet (still in the die) is lowered into the dissolution medium. In this way, a consistent surface area, the tablet face, is presented to the medium. In order to determine comparative dissolution rates of different solid forms by this method, it must first be established that solid form interconversion does not occur under the pressure used to make tablets. Therefore, tablets of SPM and SPA were prepared, removed from the die, crushed into powders, and examined by XRPD. According to XRPD analyses, no solid form interconversion occurred for either form.

Figure 1:
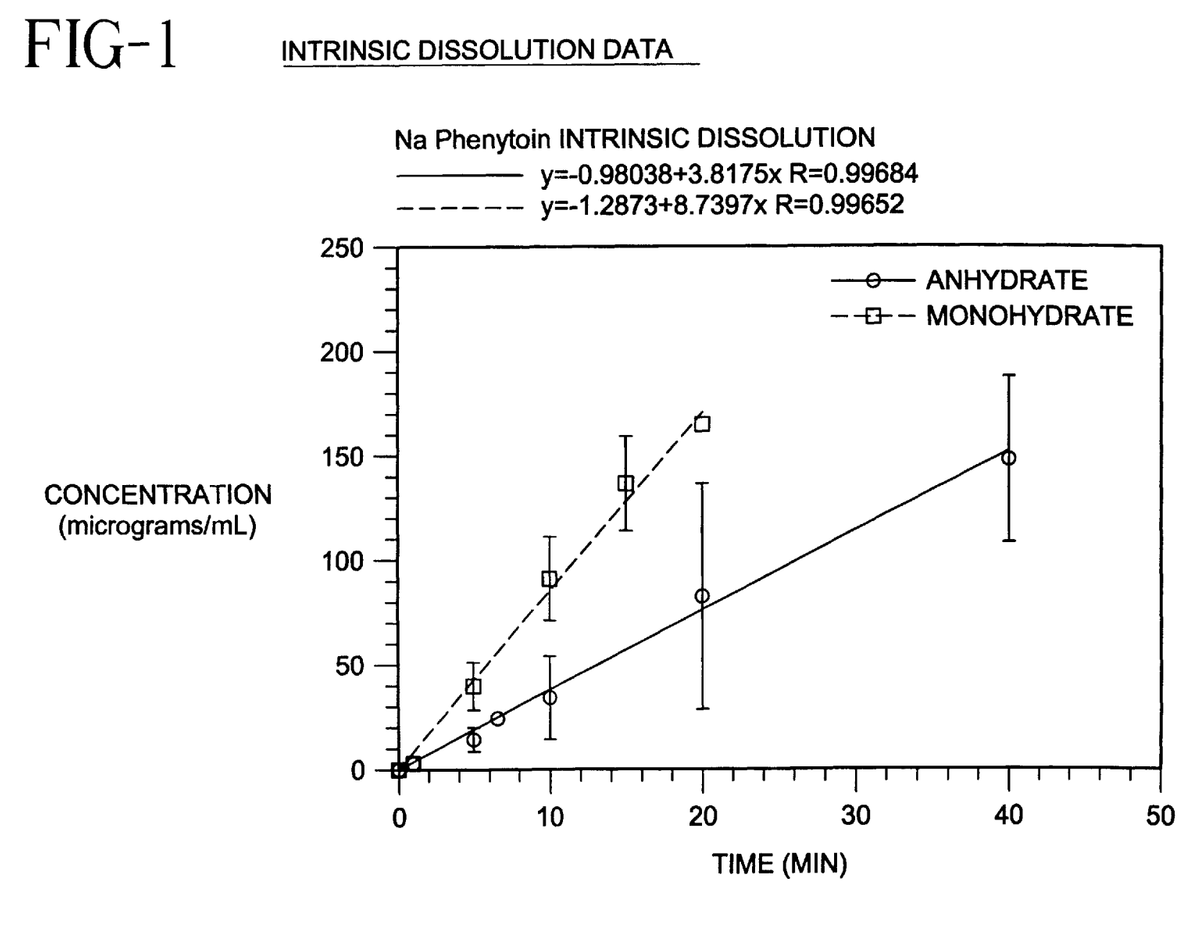
FIG. 1 shows the intrinsic dissolution rate of sodium phenytoin monohydrate (SPM) relative to sodium phenytoin anhydrate (SPA).

Intrinsic dissolution experiments were then carried out in 90% ethanol/10% water. The tablets dissolved very quickly in this medium, resulting in rapid deformation of the tablet faces. Occasionally pieces of solid broke free of the tablets and sank to the bottom of the dissolution vessel. Within 15–40 minutes the tablets had dissolved completely. Because of this behavior, consistent surface areas were not maintained during the course of the experiments. The result was a high degree of imprecision in the concentrations measured (Table 6). It appears that SPM dissolves more rapidly than does SPA, as shown in FIG. 1.

TABLE 6

Intrinsic Dissolution Results in 90% Ethanol/10% Water

| Form | Time (min) | Concentration (µg/mL) | | | | | |
|---|---|---|---|---|---|---|---|
| | | Run 1 | Run 2 | Run 3 | Average | SD[c] | RSD[d] |
| SPM[a] | 1 | 2.42 | 2.21 | 5.26 | 3.30 | 1.70 | 51.67 |
| | 5 | 44.78 | 25.24 | 48.38 | 39.46 | 12.46 | 31.54 |
| | 10 | 99.18 | 70.05 | 107.91 | 92.38 | 19.82 | 21.46 |
| | 15 | — | 120.28 | 153.22 | 136.75 | 23.29 | 17.03 |
| | 20 | 166.11 | — | — | 166.11 | — | — |
| SPA[b] | 1 | 1.73 | 1.68 | 3.36 | 2.26 | 0.96 | 42.36 |
| | 5 | 11.71 | 12.24 | 19.91 | 14.62 | 459 | 31.39 |
| | 10 | 23.27 | 23.84 | 57.43 | 34.84 | 19.56 | 56.13 |
| | 20 | 47.05 | 60.83 | 144.62 | 87.17 | 52.81 | 62.74 |
| | 40 | 112.23 | 139.74 | 193.12 | 148.36 | 41.13 | 27.72 |

[a]SPM = sodium phenytoin monohydrate.
[b]SPA = sodium phenytoin anhydrate.
[c]Absolute standard deviation.
[d]Relative standard deviation.

EXAMPLE 8

Methods were developed to determine, by X-ray powder diffraction (XRPD), the amount of SPM in SPA. Both SPM and SPA were sieved for use in quantitative method development. By using materials of the same particle size, demixing of mixtures prepared as standards will be minimized. In addition, use of small particle size materials will minimize preferred orientation effects.

SPM and SPA were each passed through a sieve stack. The SPM was somewhat, agglomerated, so large pieces were gently broken up before it was sieved. The sieve sizes and fractions collected are shown in Tables 7 and 8.

TABLE 7

Sieve Fractions Obtained of SPM

| Fraction No. | Particle Size (µm) | Weight (g) |
|---|---|---|
| Starting Material (sample 34-89-3) | | 93.7 |
| 34-97-4 | >300 | 30.8 |
| 34-97-5 | 300–212 | 12.7 |
| 34-97-6 | 212–150 | 7.79 |
| 34-97-7 | 150–106 | 6.31 |

TABLE 7-continued

Sieve Fractions Obtained of SPM

| Fraction No. | Particle Size (μm) | Weight (g) |
|---|---|---|
| 34-97-8 | 106–75 | 3.25 |
| 34-97-9 | <75 | 30.5 |
| Total weight recovered | | 91.4 |

TABLE 8

Sieve Fractions Obtained of SPA

| Fraction No. | Particle Size (μm) | Weight (g) |
|---|---|---|
| Starting Material (lot T32771) | | 102.7 |
| 34-85-1 | >300 | 0.29 |
| 34-85-2 | 300–212 | 0.0024 |
| 34-85-3 | 212–150 | 0.78 |
| 34-85-4 | 150–106 | 2.42 |
| 34-85-5 | 106–75 | 5.52 |
| 34-85-6 | <75 | 92.7 |
| Total weight recovered | | 101.7 |

Mixtures were prepared using fractions of particle size <75 μm. These are listed in Table 9.

TABLE 9

SPM/SPA Mixtures

| Sample No. | Amount SPM (mg) | Amount SPA (mg) | Percent SPM in SPA |
|---|---|---|---|
| 39-3-1 | 0 | 100 | 0 |
| 39-3-2 | 11.2 | 212.7 | 5.0 |
| 39-3-3 | 22.7 | 163.3 | 10.0 |
| 39-3-4 | 45.2 | 180.8 | 20.0 |
| 39-3-5 | 67.5 | 157.5 | 30.0 |

Each mixture was analyzed by XRPD from 4–40 °2θ at a scan rate of 2°/minute. The resulting patterns were examined carefully to identify angular regions at which the peak heights varied in the order expected from the sample compositions.

Each mixture was then reanalyzed as follows: A weighed portion (about 150 mg) was loaded into the well of an aluminum sample holder. The weight was chosen to fill the holder well, which is 15×16×1 mm. The sample was scanned three times at 0.5°/minute over the region 11.4–12.6 °2θ. The sample was removed from the holder, reweighed, reloaded into the holder, and scanned three more times as above.

The peak height at 11.9 °2θ was determined by electronic subtraction of background counts and measurement of the intensity at the highest point of the remaining peak. The six measurements at each angle were divided by the weight of the samples that produced them and averaged. Thus each mixture afforded a value of peak height/weight (counts-per-second/mg, CPS/mg) for each of three peaks. These data are shown in Table 10.

TABLE 10

Peak Height Data Obtained for Mixtures of SPM in SPA

| Sample No. | Percent SPM | CPS/mg[a] at 11.9 °2θ | SD[b] at 11.9 °2θ |
|---|---|---|---|
| 39-3-1 | 0 | 0.14 | 0.09 |
| 39-3-2 | 5.0 | 2.22 | 0.12 |
| 39-3-3 | 10.0 | 4.38 | 0.24 |
| 39-3-4 | 20.0 | 8.75 | 0.28 |
| 39-3-5 | 30.0 | 13.06 | 0.15 |

Figure 2:
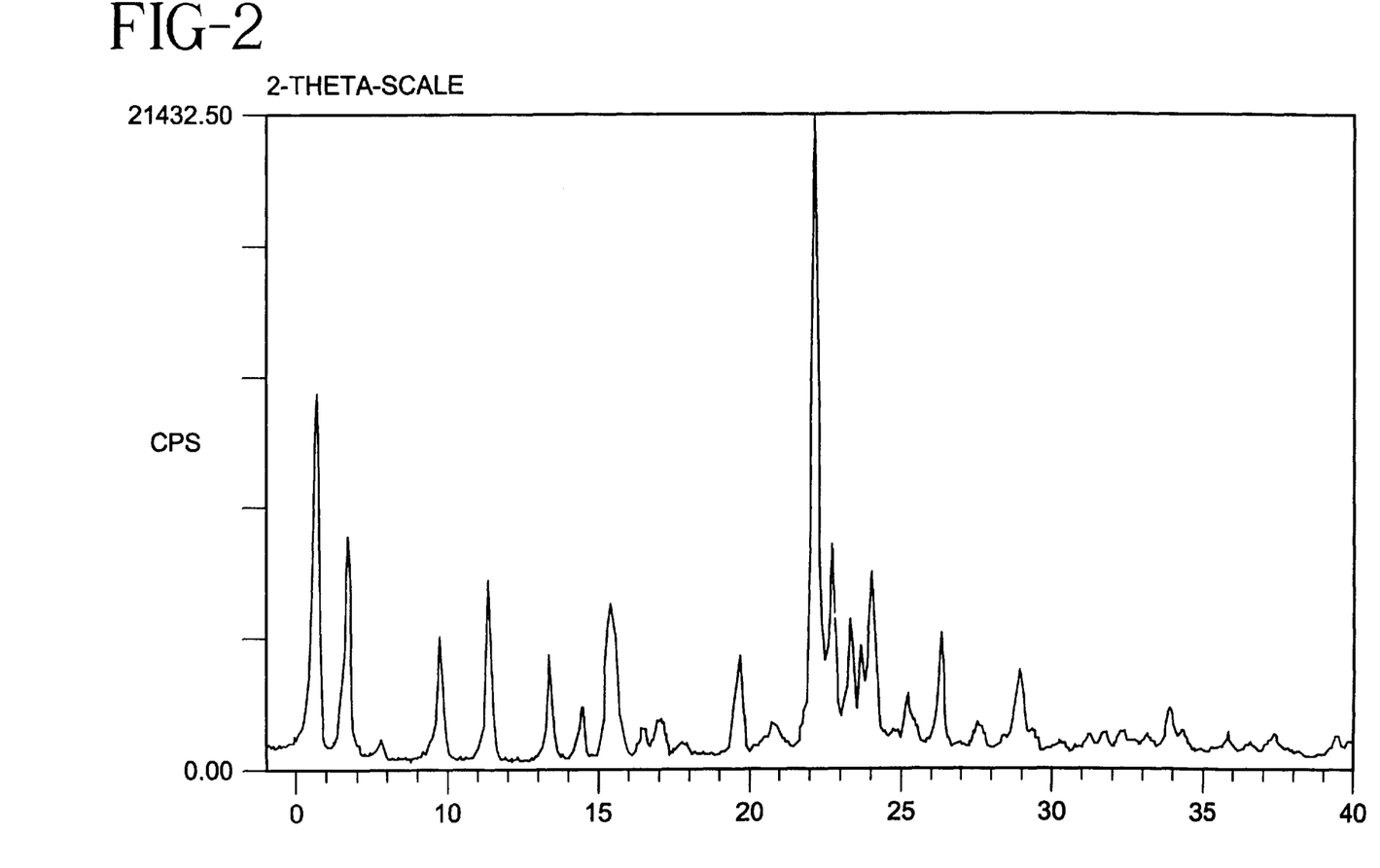
FIG. 2 is the x-ray powder diffraction pattern on the 2-theta scale for sodium phenytoin anhydrate.
Figure 3:
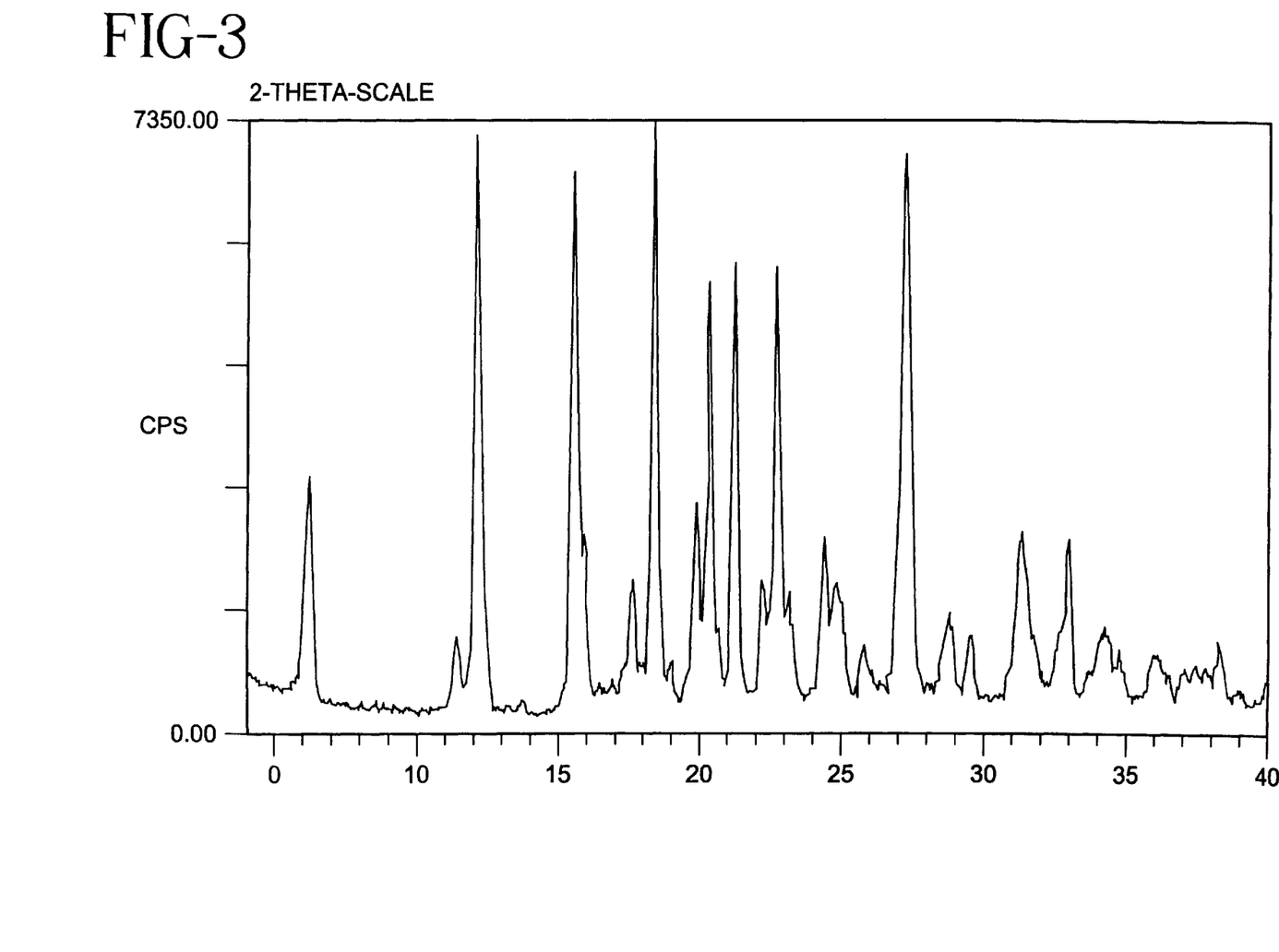
FIG. 3 is the x-ray powder diffraction pattern on the 2-theta scale for sodium phenytoin monohydrate.
Figure 4:
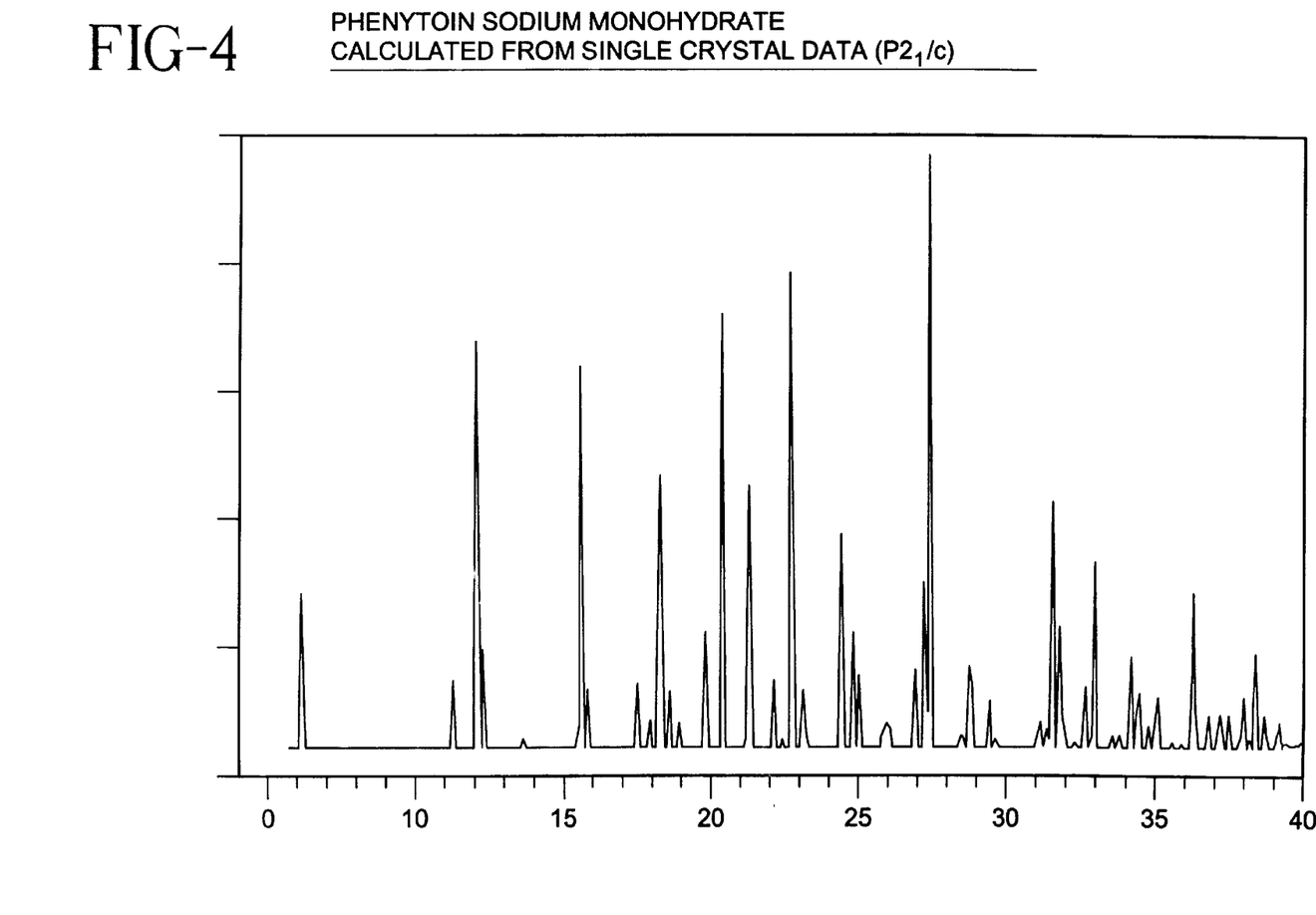
FIG. 4 is the x-ray pattern of sodium phenytoin monohydrate calculated from single crystal data ($P2_1/c$).

A series of thirty measurements were made of background counts by scanning the region 11.4–12.6 °2θ for the sample of pure SPA. Backgrounds were electronically subtracted, the resulting numbers were averaged and divided by the weight of the sample to give a intensity/weight value of 0.16 counts-per-second/mg with a standard deviation of 0.10. The limit of detection (LOD) and limit of quantification (LOQ) were calculated as follows:

minimum detectable signal=0.16+3(0.10)=0.46 cps from the line equation of FIG. 2, percent SPM=(0.46−0.094224)÷0.43198=0.85% therefore, LOD=0.85% SPM in SPA minimum quantifiable signal=0.16+10(0.10)=1.16 cps from the line equation of FIG. 2, percent SPM=(1.16−0.094224)÷0.43198=2.5% therefore, LOQ=2.5% SPM in SPA

EXAMPLE 9

Samples were analyzed by high-performance liquid chromatography (HPLC) on a BAS 480 HPLC system equipped with a UV/VIS detector and a TSP AS 100 autosampler, and controlled with INJECT software. A Phenomenex Hypersil C18 BDS column (5μ particle size, 4.6×150 mm) was used. The mobile phase was prepared by mixing water, methanol, and acetic acid in a 60:40:0.5 volume ratio. Analyses were carried out at a flow rate of 1 mL/minute with the UV/VIS detector set at 254 nm. The injection volume was 5 μL.

A calibration curve was constructed by making samples of known concentrations and analyzing them by HPLC. The data are shown in Table 11.

TABLE 11

HPLC Calibration Curve

| Sample No. | Sodium Phenytoin Concentration (mg/mL) | Peak Area |
|---|---|---|
| 22-85-5 | 0 | 0 |
| 22-85-4 | 18.7 | 54225 |
| 22-85-3 | 37.4 | 106197 |
| 22-85-2 | 74.8 | 212013 |
| 22-85-1 | 187.0 | 532380 |

A standard solution consisting of 74.8 μg/mL of sodium phenytoin in mobile phase was injected three times before and three times after each series of analyses. Each unknown sample was injected three times without dilution. The peak areas at 254 nm were recorded and averaged for each time point. The amount of sodium phenytoin in solution at each time point was calculated from the line equation of the calibration curve:

concentration (μg/mL)=(peak area−90.528)÷2844.8

EXAMPLE 10

Single Crystal Crystallography

Crystalline sodium phenytoin monohydrate was prepared as described in Example 4. The product was recrystallized several times in order to provide a pure large crystal of SPM (referred to below as $C_{15}H_{13}NaN_2O_3$ and/or $C_{15}H_{11}N_2NaO_2 \cdot H_2O$).

Data Collection

A colorless plate Of $C_{15}H_{13}NaN_2O_3$ having approximate dimensions of 0.25×0.17×0.06 mm was mounted on a glass fiber in a random orientation. Preliminary examination and data collection were performed with Cu Kα radiation (λ=1.54184 Å) on an Enraf-Nonius CAD4 computer controlled kappa axis diffractometer equipped with a graphite crystal, incident beam monochromator.

Cell constants and an orientation matrix for data collection were obtained from least-squares refinement, using the setting angles of 25 reflections in the range 15<θ<11°, measured by the computer controlled diagonal slit method of centering. The monoclinic cell parameters and calculated volume are:

a=15.526(3), b=6.206(2), c=15.799(3)Å, β=115.50(2)°, V=1374.0 Å$^3$.

For Z=4 and $M_r$=292.27 the calculated density is 1.41 g·cm$^{-3}$. As a check on crystal quality, omega scans of several intense reflections were measured; the width at half-height was 0.82° with a take-off angle of 3.0° indicating moderate crystal quality. From the systematic absences of:

h0l l=2n

0k0 k=2n and from subsequent least-squares refinement, the space group was determined to be P2$_1$/c (No. 14).

The data were collected at a temperature of 173±1 K using the ω-2θ scan technique. The scan rate varied from 1 to 16°/min (in omega). The variable scan rate allows rapid data collection for intense reflections where a fast scan rate is used and assures good counting statistics for weak reflections where a slow scan rate is used. Data were collected to a maximum 2θ of 136.3°. The scan range (in deg.) was determined as a function of θ to correct for the separation of the Kα doublet (ref 1); the scan width was calculated as follows:

ω scan width=0.82+0.330 tanθ

Moving-crystal moving-counter background counts were made by scanning an additional 25% above and below this range. Thus, the ratio of peak counting time to background counting time was 2:1. The counter aperture was also adjusted as a function of θ. The horizontal aperture width ranged from 2.4 to 3.8 mm; the vertical aperture was set at 4.0 mm. The diameter of the incident bear collimator was 0.7 mm and the crystal to detector distance was 21 cm. For intense reflections an attenuator was automatically inserted in front of the detector; the attenuator factor was 25.6.

Data Reduction

A total of 2680 reflections were collected, of which 2831 were unique.

Lorentz and polarization corrections were applied to the data. The linear absorption coefficient is 10.6 /cm for Cu Kα radiation. No absorption correction was made. Intensities of equivalent reflections were averaged. Six reflections were rejected from the averaging process because their intensities differed significantly from the average. The agreement factors for the averaging of the 132 observed and accepted reflections was 2.5% based on intensity and 2.2% based on $F_o$.

Structure Solution and Refinement

The structure was solved using the structure solution program SHELX-86 (ref 2). The remaining atoms were located in succeeding difference Fourier syntheses. Except as noted in the table of positional parameters, hydrogen atoms were located and added to the structure factor calculations but not refined. The structure was refined in full-matrix least-squares where the function minimized was $\Sigma w(|F_o|-|F_c|)^2$ and the weight w is defined as per the Killean and Lawrence method with terms of 0.020 and 1.0 (ref 3).

Scattering factors were taken from Cromer and Waber (ref 4). Anomalous dispersion effects were included in $F_c$ (ref 5): the values for $f'$ and $f''$ were those of Cromer (ref 6). Only the 1449 reflections having intensities greater than 3.0 times their standard deviation were used in the refinements. The final cycle of refinement included 202 variable parameters and converged (largest parameter shift was 0.24 times its esd) with unweighted and weighted agreement factors of:

$$R_1 = \frac{\sum ||F_o|-|F_c||}{\sum |F_o|} = 0.049$$

$$R_2 = \sqrt{\frac{\sum w(F_o - F_c)^2}{\sum wF_o^2}} = 0.067$$

The standard deviation of an observation of unit weight was 1.83. There were 24 correlation coefficients greater than 0.50. The highest correlation coefficient was 0.60 between parameters 52 and 54. The highest peak in the final difference Fourier had a height of 0.75 e·Å$^{-3}$ with an estimated error based on δF (ref 7) of 0.07. The minimum negative peak had a height of −0.18 e·Å$^{-3}$ with an estimated error based on δF of 0.07. Plots of $\Sigma w(|F_o|-|F_c|)^2$ versus $|F_o|$, reflection order in data collection, sinθ/ω, and various classes of indices showed no unusual trends.

All calculations were performed on a VAX computer. Refinement was done using MolEN (ref 8). Crystallographic drawings were done using programs OR TEP (ref 9) and/or PLUTON (ref 10).

CRYSTALLOGRAPHIC DATA FOR $C_{15}H_{11}N_2NaO_2 \cdot H_2O$

| | |
|---|---|
| NaO$_3$N$_2$C$_{15}$H$_{13}$ | formula weight 292.27 |
| a = 15.526(3)Å | space group P2$_1$/c (No. 14) |
| b = 6.206(2)Å | T = 173 K |
| c = 15.799(3)Å | λ = 1.54184Å |
| β = 115.50(2) | $D_{calc}$ = 1.413 g·cm$^{-3}$ |
| V = 1374(1)Å$^3$ | μ = 10.59 cm$^{-1}$ |
| Z = 4 | $R(F_O)^a$ = 0.049 |
| | $R_W(F_O)^b$ = 0.067 |

$$a_R = \frac{\sum ||F_o|-|F_c||}{\sum |F_o|}$$

$$b_{R_W} = \sqrt{\frac{\sum w(|F_o|-|F_c|)^2}{\sum w|F_o|^2}}$$

| CRYSTAL DATA AND DATA COLLECTION PARAMETERS FOR $C_{15}H_{13}N_2NaO_2 \cdot H_2O$ | |
|---|---|
| formula | $NaO_3N_2C_{15}H_{13}$ |
| formula weight | 292.27 |
| space group | $P2_1/c$ (No. 14) |
| a | 15.526(3) Å |
| b | 6.206(2) Å |
| c | 15.799(3) Å |
| β | 115.50(2)° |
| V | 1374(1) Å$^{-3}$ |
| Z | 4 |
| $D_{calc}$ | 1.413 g · cm$^{-3}$ |
| crystal dimensions | 0.25 × 0.17 × 0.06 mm |
| temperature | 173 K. |
| radiation (wavelength) | Cu Kα(1.54184 Å) |
| monochromator | graphite |
| linear abs coef | 1.059 mm$^{-1}$ |
| absorption correction applied | none |
| diffractometer | Enraf-Nonius CAD4 |
| scan method | ω-2θ |
| h, k, l range | −17 to 18, −7 to 0, −19 to 0 |
| 2θrange | 5.56–136.26° |
| scan width | 0.82 + 0.33 tanθ |
| take-off angle | 6.00° |
| programs used | Enraf-Nonius MolEN |
| $F_{000}$ | 608.0 |
| p-factor used in weighting | 0.040 |
| data collected | 2680 |
| unique data | 2831 |
| $R_{int}$ | 0.025 |
| data with I > 3.0 σ(I) | 1449 |
| number of variables | 202 |
| largest shift/esd in final cycle | 0.24 |
| $R(F_o)$ | 0.049 |
| $R_w(F_o)$ | 0.067 |
| goodness of fit | 1.831 |

[a]Flack H.D. Acta Crystallogr., Sect. A, A39, 876 (1983).

| Positional Parameters and Their Estimated Standard Deviations for $C_{15}H_{11}N_2NaO_2 \cdot H_2O$ | | | | |
|---|---|---|---|---|
| Atom | x | y | z | U(Å$^2$) |
| Na | 0.97607(9) | 0.0179(3) | 0.3015(1) | 0.0316(4) |
| O2 | 0.8076(2) | −0.0403(4) | 0.3437(2) | 0.0345(8) |
| O5 | 0.9334(2) | −0.6319(5) | 0.2681(2) | 0.0316(7) |
| O100 | 1.0613(3) | 0.1041(7) | 0.4512(3) | 0.093(2) |
| N1 | 0.8879(2) | −0.2958(5) | 0.2989(2) | 0.0242(8) |
| N4 | 0.8027(2) | −0.5897(5) | 0.3007(2) | 0.0229(8) |
| C2 | 0.8187(3) | −0.2284(6) | 0.3231(2) | 0.024(1) |
| C3 | 0.7533(2) | −0.4171(6) | 0.3235(2) | 0.0195(9) |
| C5 | 0.8789(2) | −0.5134(6) | 0.2882(2) | 0.023(1) |
| C31 | 0.7501(2) | −0.4451(6) | 0.4191(2) | 0.022(1) |
| C32 | 0.7060(3) | −0.2986(8) | 0.4534(3) | 0.052(1) |
| C33 | 0.7040(3) | −0.3245(9) | 0.5404(3) | 0.057(2) |
| C34 | 0.7446(3) | −0.4921(8) | 0.5926(2) | 0.043(1) |
| C35 | 0.7871(5) | −0.6411(9) | 0.5588(3) | 0.077(2) |
| C36 | 0.7904(4) | −0.6151(8) | 0.4727(3) | 0.059(2) |
| C37 | 0.6565(2) | −0.3846(6) | 0.2490(2) | 0.022(1) |
| C38 | 0.6129(3) | −0.5512(7) | 0.1889(2) | 0.032(1) |
| C39 | 0.5252(3) | −0.5233(8) | 0.1209(3) | 0.041(1) |
| C310 | 0.4796(3) | −0.3291(9) | 0.1108(3) | 0.045(1) |
| C311 | 0.5209(3) | −0.1640(8) | 0.1688(3) | 0.042(1) |
| C312 | 0.6088(3) | −0.1883(7) | 0.2372(2) | 0.030(1) |
| H4 | 0.794(2) | −0.727(6) | 0.306(2) | 0.03(1)* |
| H32 | 0.6753(7) | −0.178(2) | 0.4175(5) | 0.085 |
| H33 | 0.6739(7) | −0.221(2) | 0.5614(6) | 0.093 |
| H34 | 0.7441(6) | −0.510(2) | 0.6508(5) | 0.072 |
| H35 | 0.817(1) | −0.760(2) | 0.5964(6) | 0.114 |
| H36 | 0.8199(8) | −0.719(2) | 0.4514(6) | 0.093 |
| H38 | 0.6435(5) | −0.683(1) | 0.1953(5) | 0.058 |
| H39 | 0.4942(5) | −0.635(2) | 0.0804(6) | 0.072 |
| H101 | 1.112(6) | 0.12(2) | 0.498(6) | 0.22(4)* |
| H102 | 1.048(3) | −0.02(1) | 0.490(4) | 0.11(2)* |
| H310 | 0.4183(6) | −0.313(2) | 0.0625(6) | 0.077 |
| H311 | 0.4889(6) | −0.033(2) | 0.1615(6) | 0.074 |
| H312 | 0.6379(5) | −0.074(1) | 0.2773(5) | 0.061 |

Starred atoms were refined isotropically $$U_{eq} = \frac{1}{3}\sum_{I}\sum_{j} U_{ij}a_i^* a_j^* a_i \cdot a_j$$

Hydrogens included in calculation of structure factors but not refined $B_{isoH} = 1.3 B_{isoC}$

| Anisotropic Temperature Factor Coefficients - B's for $C_{15}H_{11}N_2NaO_2 \cdot H_2O$ | | | | | | | |
|---|---|---|---|---|---|---|---|
| Name | $B_{11}$ | $B_{22}$ | $B_{33}$ | $B_{12}$ | $B_{13}$ | $B_{23}$ | $B_{eqv}$ |
| Na | 2.44(5) | 2.20(6) | 3.38(5) | −0.33(5) | 1.76(3) | −0.37(5) | 0.0316(4) |
| O2 | 3.21(10) | 1.42(11) | 3.47(10) | −0.29(9) | 1.38(8) | −0.46(9) | 0.0345(8) |
| O5 | 2.20(8) | 2.78(13) | 3.17(9) | 0.31(9) | 1.79(6) | 0.01(9) | 0.0316(7) |
| O100 | 8.0(2) | 7.4(2) | 3.55(16) | 1.0(2) | −0.39(16) | −1.35(17) | 0.0931(17 |
| N1 | 1.94(10) | 1.65(13) | 2.44(10) | −0.34(10) | 1.22(8) | 0.19(10) | 0.0242(8) |
| N4 | 1.92(9) | 1.25(12) | 2.92(10) | −0.24(10) | 1.68(7) | −0.23(10) | 0.0229(8) |
| C2 | 2.35(13) | 1.62(15) | 1.45(12) | −0.07(13) | 0.51(9) | −0.09(12) | 0.0242(10 |
| C3 | 1.62(11) | 1.63(15) | 1.54(11) | 0.09(12) | 0.84(8) | 0.08(12) | 0.0195(9) |
| C5 | 1.81(11) | 2.17(16) | 1.48(11) | 0.16(11) | 0.68(8) | 0.37(13) | 0.0231(1) |
| C31 | 1.72(11) | 2.07(16) | 1.45(12) | −0.17(12) | 0.73(8) | −0.02(12) | 0.0219(10 |
| C32 | 5.01(18) | 5.3(2) | 2.56(14) | 3.01(18) | 2.23(11) | 1.09(17) | 0.0518(14 |
| C33 | 4.65(17) | 7.1(3) | 2.46(14) | 2.3(2) | 2.13(11) | 0.50(19) | 0.0571(15 |
| C34 | 4.39(17) | 4.2(2) | 1.69(13) | −0.75(18) | 1.41(11) | 0.06(16) | 0.0431(13 |
| C35 | 11.8(3) | 3.8(2) | 2.62(16) | 2.2(3) | 3.12(17) | 1.13(18) | 0.077(2) |
| C36 | 8.7(3) | 3.1(2) | 2.25(15) | 2.4(2) | 2.44(14) | 0.72(16) | 0.0589(16 |
| C37 | 1.88(11) | 2.14(16) | 1.52(11) | −0.19(12) | 1.05(8) | 0.01(12) | 0.0220(10 |

-continued

Anisotropic Temperature Factor Coefficients - B's for $C_{15}H_{11}N_2NaO_2 \cdot H_2O$

| Name | $B_{11}$ | $B_{22}$ | $B_{33}$ | $B_{12}$ | $B_{13}$ | $B_{23}$ | $B_{eqv}$ |
|---|---|---|---|---|---|---|---|
| C38  | 2.53(13) | 3.2(2)   | 1.89(12) | −0.53(15) | 1.12(9)  | −0.05(14) | 0.0316(11 |
| C39  | 2.63(14) | 5.0(2)   | 1.76(13) | −1.22(17) | 0.57(11) | −0.28(16) | 0.0412(13 |
| C310 | 2.05(14) | 6.0(3)   | 2.28(14) | −0.37(1.8) | 0.61(11) | 0.68(17)  | 0.0452(14 |
| C311 | 2.35(13) | 5.0(2)   | 2.75(14) | 1.38(16)  | 1.30(10) | 1.20(16)  | 0.0419(13 |
| C312 | 2.37(13) | 2.99(19) | 2.00(12) | 0.57(14)  | 1.09(9)  | 0.21(14)  | 0.0304(11 |

The form of the anisotropic temperature factor is:

$$\exp[-0.25(h^2 a^{*2} B_{11} + k^2 b^{*2} B_{22} + l^2 c^{*2} B_{33} + 2hKa^* b^* B_{12} + 2hla^* c^* B_{13} + 2klb^* c^* B_{23})]$$

where $a^*$, $b^*$, and $c^*$ are reciprocal lattice constants.

Table of Refined Temperature Factor Expressions - Beta's for $C_{15}H_{11}N_2NaO_2 \cdot H_2O$

| Name | $B_{11}$ | $B_{22}$ | $B_{33}$ | $B_{12}$ | $B_{13}$ | $B_{23}$ | |
|---|---|---|---|---|---|---|---|
| Na   | 0.00310(6)  | 0.0143(4)  | 0.00416(6)  | −0.0019(3)  | 0.00440(9)  | −0.0021(3)  | 04(11) |
| O2   | 0.00408(13) | 0.0092(7)  | 0.00427(13) | −0.0017(5)  | 0.00344(19) | −0.0026(5)  | 04(11) |
| O5   | 0.00280(10) | 0.0180(8)  | 0.00390(11) | 0.0018(5)   | 0.00448(15) | 0.0001(5)   | 04(11) |
| O100 | 0.0102(3)   | 0.0483(16) | 0.00437(19) | 0.0059(12   | −0.0010(4)  | −0.0076(10) | 04(11) |
| N1   | 0.00247(12) | 0.0107(8)  | 0.00300(13) | −0.0019(6)  | 0.00306(19) | 0.0010(6)   | 04(11) |
| N4   | 0.00245(12) | 0.0081(8)  | 0.00359(13) | −0.0014(6)  | 0.00421(18) | −0.0013(6)  | 04(11) |
| C2   | 0.00299(16) | 0.0105(10) | 0.00178(14) | −0.0004(7)  | 0.0013(2)   | −0.0005(7)  | 04(11) |
| C3   | 0.00207(13) | 0.0106(10) | 0.00190(13) | 0.0005(7)   | 0.0021(2)   | 0.0004(7)   | 04(11) |
| C5   | 0.00230(14) | 0.0141(11) | 0.00181(13) | 0.0009(8)   | 0.0017(2)   | 0.0021(7)   | 04(11) |
| C31  | 0.00220(14) | 0.0134(11) | 0.00178(13) | −0.0010(7)  | 0.0018(2)   | −0.0001(7)  | 04(11) |
| C32  | 0.0064(2)   | 0.0346(16) | 0.00314(17) | 0.0173(10   | 0.0056(3)   | 0.0061(9)   | 04(11) |
| C33  | 0.0059(2)   | 0.046(2)   | 0.00302(17) | 0.0132(12   | 0.0053(3)   | 0.0028(11)  | 04(11) |
| C34  | 0.0056(2)   | 0.0275(14) | 0.00208(16) | −0.0043(10  | 0.0035(3)   | 0.0003(9)   | 04(11) |
| C35  | 0.0150(4)   | 0.0246(16) | 0.0032(2)   | 0.0127(15   | 0.0078(4)   | 0.0064(10)  | 04(11) |
| C36  | 0.0111(3)   | 0.0198(14) | 0.00277(18) | 0.0140(12   | 0.0061(4)   | 0.0041(9)   | 04(11) |
| C37  | 0.00240(14) | 0.0139(11) | 0.00187(13) | −0.0011(7)  | 0.0026(2)   | 0.0000(7)   | 04(11) |
| C38  | 0.00322(16) | 0.0211(13) | 0.00233(15) | −0.0031(9)  | 0.0028(2)   | −0.0003(8)  | 04(11) |
| C39  | 0.00335(18) | 0.0322(16) | 0.00217(16) | −0.0070(10  | 0.0014(3)   | −0.0016(9)  | 04(11) |
| C310 | 0.00261(18) | 0.0392(18) | 0.00280(18) | −0.0022(10  | 0.0015(3)   | 0.0038(10)  | 04(11) |
| C311 | 0.00299(17) | 0.0328(16) | 0.00339(17) | 0.0079(9)   | 0.0033(3)   | 0.0068(9)   | 04(11) |
| C312 | 0.00302(16) | 0.0194(12) | 0.00246(15) | 0.0033(8)   | 0.0027(2)   | 0.0012(8)   | 04(11) |

The form of the anisotropic temperature factor is:

$$\exp[-(\beta_{11}h^2 + {}_{22}k^2 + \beta_{33}l^2 + {}_{12}hk + \beta_{13}hl + {}_{23}kl)].$$

Anisotropic Temperature Factor Coefficients - U's for $C_{15}H_{11}N_2NaO_2 \cdot H_2O$

| Name | $B_{11}$ | $B_{22}$ | $B_{33}$ | $B_{12}$ | $B_{13}$ | $B_{23}$ | |
|---|---|---|---|---|---|---|---|
| Na   | 0.0309(6)  | 0.0278(8)  | 0.0429(6)  | −0.0041(6)  | 0.0223(4)  | −0.0046(7)  | 04(11) |
| O2   | 0.0406(13) | 0.0180(14) | 0.0440(13) | −0.0037(12) | 0.0174(10) | −0.0058(12) | 04(11) |
| O5   | 0.0279(10) | 0.0352(16) | 0.0402(11) | 0.0040(11)  | 0.0227(8)  | 0.0002(12)  | 04(11) |
| O100 | 0.101(3)   | 0.094(3)   | 0.045(2)   | 0.013(3)    | −0.005(2)  | −0.017(2)   | 04(11) |
| N1   | 0.0245(12) | 0.0209(16) | 0.0309(13) | −0.0043(13) | 0.0155(10) | 0.0023(13)  | 04(11) |
| N4   | 0.0243(11) | 0.0158(15) | 0.0370(13) | −0.0031(12) | 0.0213(9)  | −0.0029(13) | 04(11) |
| C2   | 0.0297(16) | 0.0205(19) | 0.0184(15) | −0.0009(16) | 0.0065(12) | −0.0012(15) | 04(11) |
| C3   | 0.0205(13) | 0.0206(19) | 0.0195(14) | 0.0012(15)  | 0.0107(10) | 0.0010(15)  | 04(11) |
| C5   | 0.0229(14) | 0.028(2)   | 0.0187(14) | 0.0020(17)  | 0.0087(11) | 0.0046(16)  | 04(11) |
| C31  | 0.0218(14) | 0.026(2)   | 0.0183(14) | −0.0021(16) | 0.0092(10) | −0.0003(15) | 04(11) |
| C32  | 0.063(2)   | 0.067(3)   | 0.0324(18) | 0.038(2)    | 0.0282(14) | 0.014(2)    | 04(11) |

-continued

Anisotropic Temperature Factor Coefficients - U's for $C_{15}H_{11}N_2NaO_2 \cdot H_2O$

| Name | $B_{11}$ | $B_{22}$ | $B_{33}$ | $B_{12}$ | $B_{13}$ | $B_{23}$ | |
|---|---|---|---|---|---|---|---|
| C33 | 0.059(2) | 0.089(4) | 0.0311(18) | 0.029(3) | 0.0270(14) | 0.006(2) | 04(11) |
| C34 | 0.056(2) | 0.054(3) | 0.0214(16) | −0.010(2) | 0.0179(14) | 0.001(2) | 04(11) |
| C35 | 0.149(4) | 0.048(3) | 0.033(2) | 0.028(3) | 0.040(2) | 0.014(2) | 04(11) |
| C36 | 0.110(3) | 0.039(3) | 0.0286(19) | 0.031(3) | 0.0309(18) | 0.009(2) | 04(11) |
| C37 | 0.0239(14) | 0.027(2) | 0.0192(13) | −0.0024(16) | 0.0133(10) | 0.0001(15) | 04(11) |
| C38 | 0.0320(16) | 0.041(3) | 0.0240(16) | −0.0067(19) | 0.0142(12) | −0.0006(17) | 04(11) |
| C39 | 0.0333(18) | 0.063(3) | 0.0223(17) | −0.015(2) | 0.0072(13) | −0.004(2) | 04(11) |
| C310 | 0.0260(17) | 0.077(3) | 0.0289(18) | −0.005(2) | 0.0077(14) | 0.009(2) | 04(11) |
| C311 | 0.0297(17) | 0.064(3) | 0.0349(18) | 0.018(2) | 0.0165(13) | 0.015(2) | 04(11) |
| C312 | 0.0301(16) | 0.038(2) | 0.0253(16) | 0.0072(17) | 0.0138(12) | 0.0027(17) | 04(11) |

The form of the anisotropic temperature factor is:

$$\exp[-2\pi(h^2 a^{*2} U_{11} + k^2 b^{*2} U_{22} + l^2 c^{*2} U_{33} + 2hk a^* b^* U_{12} + 2hl a^* c^* U_{13} + 2kl b^* c^* U_{23})]$$

where a*, b*, and c* are reciprocal lattice constants.

Table of Bond Distances in Angstroms for $C_{15}H_{11}N_2NaO_2 \cdot H_2O$

| | Distance | | Distance |
|---|---|---|---|
| Na—O5 | 2.267(3) | C3—C31 | 1.541(5) |
| Na—O5 | 2.320(3) | C3—C37 | 1.471(5) |
| Na—O100 | 2.223(5) | C31—C32 | 1.382(6) |
| Na—N1 | 2.370(3) | C31—C36 | 1.329(6) |
| O2—C2 | 1.244(5) | C32—C33 | 1.397(6) |
| O5—C5 | 1.260(5) | C33—C34 | 1.308(7) |
| O100—H101 | 0.8(1) | C34—C35 | 1.371(7) |
| O100—H102 | 1.06(8) | C35—C36 | 1.393(7) |
| N1—C2 | 1.353(5) | C37—C38 | 1.369(5) |
| N1—C5 | 1.361(5) | C37—C312 | 1.396(6) |
| N4—C3 | 1.451(5) | C38—C39 | 1.334(6) |
| N4—C5 | 1.365(5) | C39—C310 | 1.371(7) |
| N4—H4 | 0.87(4) | C310—C311 | 1.340(7) |
| C2—C3 | 1.552(5) | C311—C312 | 1.335(6) |

Numbers in parentheses are estimated standard deviations in the least significant digits.

Table of Bond Angles in Degrees for $C_{15}H_{11}N_2NaO_2 \cdot H_2O$

| | Angle | | Angle |
|---|---|---|---|
| O5—Na—O5 | 116.8(1) | N4—C3—C37 | 111.7(3) |
| O5—Na—O100 | 89.8(2) | C2—C3—C31 | 112.7(3) |
| O5—Na—N1 | 132.4(1) | C2—C3—C37 | 109.8(3) |
| O5—Na—O100 | 113.4(2) | C31—C3—C37 | 110.3(3) |
| O5—Na—N1 | 97.2(1) | N1—C5—N4 | 112.1(4) |
| O100—Na—N1 | 106.9(2) | C3—C31—C32 | 122.7(4) |
| Na—O5—Na | 108.5(1) | C3—C31—C36 | 120.6(4) |
| Na—O5—C5 | 131.4(3) | C32—C31—C36 | 116.7(4) |
| Na—O5—C5 | 119.7(3) | C31—C32—C33 | 122.3(5) |
| Na—O100—H101 | 152(8) | C32—C33—C34 | 120.2(5) |
| Na—O100—H102 | 106(4) | C33—C34—C35 | 118.2(4) |
| H101—O100—H102 | 86(8) | C34—C35—C36 | 122.0(5) |
| Na—N1—C2 | 105.3(3) | C31—C36—C35 | 120.6(5) |
| Na—N1—C5 | 147.7(3) | C3—C37—C38 | 118.8(4) |
| C2—N1—C5 | 106.8(3) | C3—C37—C312 | 121.8(4) |
| C3—N4—C5 | 111.3(3) | C38—C37—C312 | 119.4(4) |
| C3—N4—H4 | 126(3) | C37—C38—C39 | 119.3(4) |
| C5—N4—H4 | 122(3) | C38—C39—C310 | 120.3(4) |
| N1—C2—C3 | 111.7(3) | C39—C310—C311 | 121.5(4) |
| N4—C3—C2 | 98.0(3) | C310—C311—C312 | 119.2(5) |
| N4—C3—C31 | 113.8(3) | C37—C312—C311 | 120.3(4) |

Numbers in parentheses are estimated standard deviations in the least significant digits.

Table of Torsion Angles in Degrees

| | Angle |
|---|---|
| O100—Na—N1—C2 | 72.90 (0.26) |
| O100—Na—N1—C5 | −102.12 (0.43) |
| Na—N1—C2—O2 | −1.34 (0.41) |
| Na—N1—C2—C3 | 179.34 (0.21) |
| C5—N1—C2—O2 | 175.88 (0.33) |
| C5—N1—C2—C3 | −3.44 (0.36) |
| Na—N1—C5—O5 | −3.01 (0.63) |
| Na—N1—C5—N4 | 177.75 (0.30) |
| C2—N1—C5—O5 | −177.99 (0.31) |
| C2—N1—C5—N4 | 2.77 (0.37) |
| C5—N4—C3—C2 | −1.00 (0.32) |
| C5—N4—C3—C31 | −120.23 (0.32) |
| C5—N4—C3—C37 | 114.08 (0.33) |
| H4—N4—C3—C2 | 166.43 (2.61) |
| H4—N4—C3—C31 | 47.21 (2.63) |
| H4—N4—C3—C37 | −78.49 (2.63) |
| C3—N4—C5—O5 | 179.78 (0.29) |
| C3—N4—C5—N1 | −0.97 (0.37) |
| H4—N4—C5—O5 | 11.83 (2.49) |
| H4—N4—C5—N1 | −168.92 (2.45) |
| O2—C2—C3—N4 | −176.61 (0.31) |
| O2—C2—C3—C31 | −56.58 (0.45) |
| O2—C2—C3—C37 | 66.79 (0.42) |
| N1—C2—C3—N4 | 2.73 (0.34) |
| N1—C2—C3—C31 | 122.76 (0.32) |
| N1—C2—C3—C37 | −113.87 (0.33) |
| N4—C3—C31—C32 | −179.71 (0.37) |
| N4—C3—C31—C36 | 0.13 (0.55) |
| C2—C3—C31—C32 | 69.83 (0.48) |
| C2—C3—C31—C36 | −110.33 (0.45) |
| C37—C3—C31—C32 | −53.26 (0.50) |
| C37—C3—C31—C36 | 126.58 (0.44) |
| N4—C3—C37—C38 | 22.63 (0.47) |
| N4—C3—C37—C312 | −156.39 (0.34) |
| C2—C3—C37—C38 | 130.24 (0.36) |
| C2—C3—C37—C312 | −48.77 (0.45) |
| C31—C3—C37—C38 | −104.97 (0.38) |
| C31—C3—C37—C312 | 76.01 (0.44) |

-continued

Table of Torsion Angles in Degrees

| | Angle |
|---|---|
| C3—C31—C32—C33 | −179.56 (0.42) |
| C36—C31—C32—C33 | 0.60 (0.70) |
| C3—C31—C36—C35 | −179.62 (0.47) |
| C32—C31—C36—C35 | 0.22 (0.74) |
| C31—C32—C33—C34 | −0.19 (0.77) |
| C32—C33—C36—C35 | −1.02 (0.79) |
| C33—C34—C35—C36 | 1.86 (0.87) |
| C34—C35—C36—C31 | −1.48 (0.91) |
| C3—C37—C38—C39 | −179.76 (0.36) |
| C312—C37—C38—C39 | −0.72 (0.58) |
| C3—C37—C312—C311 | 179.97 (0.38) |
| C38—C37—C312—C311 | 0.95 (0.59) |
| C37—C38—C39—C310 | 0.58 (0.63) |
| C38—C39—C31—C311 | −0.67 (0.68) |
| C39—C310—C311—C312 | 0.89 (0.68) |
| C310—C311—C312—C37 | −1.03 (0.64) |

Table of Atomic Multiplicities for $C_{15}H_{11}N_2NaO_2 \cdot H_2O$

| Name | Multiplicity | Name | Multiplicity | Name | Multiplicity |
|---|---|---|---|---|---|
| Na | 1.000 | C312 | 1.000 | H102 | 1.000 |
| N1 | 1.000 | C32 | 1.000 | H32 | 1.000 |
| N4 | 1.000 | C33 | 1.000 | H33 | 1.000 |
| O2 | 1.000 | C34 | 1.000 | H34 | 1.000 |
| O5 | 1.000 | C35 | 1.000 | H35 | 1.000 |
| O100 | 1.000 | C36 | 1.000 | H36 | 1.000 |
| C2 | 1.000 | C37 | 1.000 | H38 | 1.000 |
| C3 | 1.000 | C38 | 1.000 | H39 | 1.000 |
| C5 | 1.000 | C39 | 1.000 | H310 | 1.000 |
| C31 | 1.000 | H4 | 1.000 | H311 | 1.000 |
| C310 | 1.000 | H101 | 1.000 | H312 | 1.000 |
| C311 | 1.000 | | | | |

REFERENCES

1. "CAD4 Operations Manual", Enraf-Nonius, Delft, 1977
2. G. M. Sheldrick, SHELXS86. *A Program for the Solution of Crystal Strtuctures.*, Univ. of Gottingen, Germany, 1985.
3. R. C. G. Killean and J. L. Lawrence, *Acta Crystallogr.*, Sect B, 25, 1750 (1969).
4. D. T. Cromer and J. T. Waber, "International Tables for X-Ray Crystallography", Vol. IV, The Kynoch Press, Birmingham, England, 1974, Table 2.2B.
5. J. A. Ibers and W. C. Hamilton, *Acta Crystallogr.*, 17, 781(1964).
6. D. T. Cromer, "International Tables for X-Ray Crystallography," Vol. IV, The Kynoch Press, Birmingham, England, 1974, Table 2.3.1.
7. D. W. J. Cruickshank, *Acta Crystallogr.*, 2, 154 (1949).
8. C. K. Fair, MolEN Structure Determination System, Delft Instruments, Delft, The Netherlands (1990).
9. C. K. Johnson, *ORTEPII*, ReportORNL-5138, Oak Ridge National Laboratory, Tennessee, USA (1976).
10. A. L. Spek, *PLUTON*. Molecular Graphics Program. Univ. of Ultrecht, The Netherlands (1991).

The crystalline sodium phenytoin monohydrate provided by his invention is useful as an anticonvulsant agent, especially for treating all forms of epilepsy. The compound can be formulated for convenient oral or parenteral administration. The crystals can be admixed with conventional carriers and excipients such as sucrose, polyvinylpyrrolidone, stearic acid, starch, talc, magnesium stearate and the like, and encapsulated into gelatin capsules, or if desired, the formulation can be pressed into tablets. The crystalline monohydrate can additionally be dissolved in sterile aqueous solutions such as isotonic saline or 5% aqueous glucose for parenteral administration, for example, by intravenous infusion. The pharmaceutical formulations of this invention typically will contain from about 10% to about 90% by weight of the monohydrate, for instance from about 30 mg to about 3000 mg per dosage unit. The monohydrate can be formulated with polymers and the like that are routinely utilized to retard release so as to have slow release dosage forms.

The monohydrate of this invention can additionally be added to sodium phenytoin that is produced by commercial processes such as those described above. By adding from about 1% to about 10% by weight of the monohydrate, commercial preparations of sodium phenytoin are stabilized such that their rate of dissolution are made more uniform, thereby resulting in more consistent dosing profiles of such commercial preparations.

As noted above, the crystalline sodium phenytoin of this invention is biologically effective to control generalized tonic-clonic (grand mal) and complex partial (psychomotor, temporal lobe) seizures. The compound can be utilized alone or in combination with other anticonvulsant agents, for instance gabapentin and the like. The invention, therefore, further provides a method for treating anticonvulsant disorders in humans comprising administering an anticonvulsant effective amount of the sodium phenytoin monohydrate. Such effective amounts will be a daily dosage of from about 30 mg to about 3000 mg, and preferably about 100 mg to about 1000 mg per day for a typical adult patient.

What is claimed is:

1. Crystalline sodium phenytoin monohydrate exhibiting essentially the following x-ray diffraction data:

| 2-Theta | Spacing, d(Å) | Relative Intensities, $I/I_1$ |
|---|---|---|
| 12.129 | 7.2909 | 100.00 |
| 27.227 | 3.2727 | 80.38 |
| 22.685 | 3.9165 | 72.60 |
| 15.542 | 5.6968 | 70.76 |
| 18.379 | 4.8234 | 67.28 |
| 20.259 | 4.3798 | 59.76 |
| 21.223 | 4.1830 | 53.97 |
| 6.214 | 14.2105 | 48.83 |
| 23.158 | 3.8377 | 40.99 |
| 17.195 | 5.1526 | 36.52 |
| 20.630 | 4.3019 | 34.49 |
| 31.173 | 2.8668 | 29.10 |
| 24.337 | 3.6544 | 27.54 |
| 32.827 | 2.7260 | 27.32 |
| 19.774 | 4.4861 | 27.15 |
| 16.373 | 5.4093 | 24.13 |
| 24.700 | 3.6013 | 24.02 |
| 17.537 | 5.0528 | 22.00 |
| 31.731 | 2.8177 | 21.75 |
| 28.668 | 3.1114 | 18.17 |
| 11.363 | 7.7805 | 17.00 |
| 28.969 | 3.0797 | 15.93 |
| 33.963 | 2.6374 | 15.15 |
| 29.399 | 3.0355 | 14.73 |
| 32.540 | 2.7494 | 14.52 |
| 23.856 | 3.7269 | 14.30 |
| 34.235 | 2.6171 | 13.95 |

-continued

| 2-Theta | Spacing, d(Å) | Relative Intensities, $I/I_1$ |
|---|---|---|
| 35.808 | 2.5056 | 13.77 |
| 34.725 | 2.5812 | 13.24 |
| 28.167 | 3.1655 | 13.02 |
| 38.255 | 2.3508 | 12.60 |
| 36.386 | 2.4671 | 12.49 |
| 25.660 | 3.4687 | 12.03 |
| 26.323 | 3.3829 | 11.96 |
| 16.782 | 5.2785 | 11.75. |

2. Crystalline sodium phenytoin monohydrate exhibiting essentially the following x-ray diffraction data:

| 2-Theta | d (Å) | Relative Intensities (I) |
|---|---|---|
| 12.1 | 7.3 | 100 |
| 27.2 | 3.3 | 80 |
| 22.7 | 3.9 | 73 |
| 15.5 | 5.7 | 71 |
| 18.4 | 4.8 | 67 |
| 20.3 | 4.4 | 60 |
| 21.2 | 4.2 | 54 |
| 6.2 | 14.2 | 49 |

3. Crystalline sodium phenytoin monohydrate having an x-ray powder diffraction pattern containing the following 2-theta values measured using $CuK_\alpha$ radiation: 12.1, 18.4, and 21.2.

4. Crystalline sodium phenytoin monohydrate having an x-ray powder diffraction pattern containing the following 2-theta values measured using $CuK_\alpha$ radiation: 12.1.

5. A process for preparing sodium phenytoin monohydrate of claim 1 comprising mixing sodium phenytoin anhydrate and water in an organic solvent selected from toluene, methanol and dichloromethane, at about 30° C. to about 40° C.

6. A pharmaceutical formulation comprising the sodium phenytoin monohydrate of claim 1 together with a pharmaceutical excipient, diluent, or carrier therefor.

7. The formulation of claim 3 in the form of a capsule.

8. The formulation of claim 3 in the form of a liquid for intravenous administration.

9. A method of treating convulsant disorders in humans comprising administering an anticonvulsant effective amount of the compound of claim 1.

10. A method for stabilizing an amorphous polymorphic mixture of sodium phenytoin comprising adding a stabilizing amount of the compound of claim 1.

11. A pharmaceutical composition comprising the sodium phenytoin monohydrate of claim 3 together with a pharmaceutical excipient, diluent, or carrier therefor.

12. A pharmaceutical composition comprising the sodium phenytoin monohydrate of claim 4 together with a pharmaceutical excipient, diluent, or carrier therefor.

* * * * *